United States Patent [19]

Uno et al.

[11] 4,329,510

[45] May 11, 1982

[54] PROCESS FOR PURIFYING KETONES

[75] Inventors: Kazutoyo Uno; Hisaya Miki, both of Ichihara, Japan

[73] Assignee: Mitsui Petrochemical Industries, Ltd., Tokyo, Japan

[21] Appl. No.: 175,737

[22] Filed: Aug. 6, 1980

[30] Foreign Application Priority Data

Aug. 7, 1979 [JP] Japan ............................... 54-99902
Sep. 3, 1979 [JP] Japan ............................... 54-111723

[51] Int. Cl.$^3$ ...................... C07C 49/04; C07C 49/20
[52] U.S. Cl. .................................... 568/411; 568/410
[58] Field of Search ............... 568/411, 410; 562/324, 562/338, 343

[56] References Cited

U.S. PATENT DOCUMENTS

3,193,582  7/1965  Adams et al. ........................ 568/411
3,632,652  3/1968  Chu et al. ............................ 568/411
3,668,256  6/1972  Brundege .
3,912,778  10/1975  Alheri et al. ........................ 568/411

FOREIGN PATENT DOCUMENTS

53-137907  1/1978  Japan .
1412645  5/1975  United Kingdom .

*Primary Examiner*—Winston A. Douglas
*Assistant Examiner*—Raymond Covington
*Attorney, Agent, or Firm*—Sherman & Shalloway

[57] ABSTRACT

In a process for recovering a purified ketone substantially free from aldehydes which comprises contacting a crude ketone containing small amounts of aldehydes with an alkali and then distilling the treated crude ketone, the improvement wherein said alkali is a solid alkali composition composed of an alkali metal compound selected from alkali metal oxides and hydroxides, an alkaline earth metal compound selected from alkaline earth metal oxides and hydroxides and silicon dioxide in which the mole ratio of the alkali metal to the alkaline earth metal is in the range of from 1:1 to 1:15, and the mole ratio of the alkali metal to silicon is in the range of from 1:0.25 to 1:5.

11 Claims, No Drawings
}

PROCESS FOR PURIFYING KETONES

This invention relates to a process for purifying a crude ketone including a small amount of an aldehyde. More specifically, this invention relates to an improvement in a process which comprises pre-treating a crude ketone containing a small amount of an aldehyde with an alkali, and distilling the pre-treated ketone thereby to recover the purified ketone.

Industrially, ketones are now produced in large quantities by acid cleavage of aralkyl hydroperoxides of the following formula

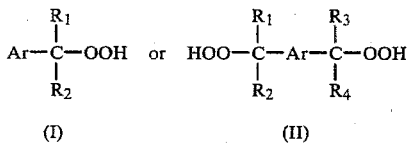

wherein Ar represents an aromatic hydrocarbon group, and $R_1$, $R_2$, $R_3$ and $R_4$, independently from each other, represent a lower alkyl group. In the acid cleavage of these aralkyl hydroperoxides, the reaction mixture comprising a ketone of the formula $R_1$—CO—$R_2$ and an aromatic alcohol of the formula Ar—OH is obtained from the aralkyl hydroperoxide of formula (I), and the reaction mixture comprising ketones of the formulae $R_1$—CO—$R_2$ and $R_3$—CO—$R_4$ and an aromatic alcohol of the formula HO—Ar—OH is obtained from the aralkyl hydroperoxide of formula (II). The reaction mixture is then distilled to separate it into an overhead fraction consisting substantially of the ketone and a bottom fraction consisting of the aromatic alcohol and other high-boiling compounds. It is well known generally that the overhead fraction is a crude ketone containing small amounts of aliphatic aldehydes formed as by-products during the acid cleavage.

For example, the reaction mixture obtained by acid cleavage of cumene hydroperoxide of the formula

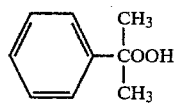

contains acetone and phenol and minor amounts of aliphatic aldehydes such as acetaldehyde, propionaldehyde, n-butyraldehyde and isobutyraldehyde. When the crude acetone obtained by distilling this acid cleavage reaction mixture is distilled in a known manner, the aldehydes still remain in the purified acetone to reduce its purity and quality. As an attempt to remove such a defect, U.S. Pat. No. 3,668,256 describes in the BACKGROUND OF INVENTION a process which comprises pre-treating the crude acetone containing small amounts of the aldehydes with an aqueous alkali solution to convert the aldehydes to higher boiling condensates by aldol condensation, and distilling the pre-treated crude acetone to collect the acetone fraction and discharge the aldehydes as high-boiling distillation bottoms.

However, this suggested process involving aldol condensation with an aqueous alkali solution has the defect that when the temperature at which the pre-treated crude acetone is distilled is elevated in order to increase the ratio of its recovery, de-condensation reaction of the high-boiling condensates takes place to form the corresponding aldehydes which in turn will get mixed with the acetone fraction. In order to avoid this trouble, it is necessary to maintain a low distillation temperature and a high acetone concentration of the distillation bottoms. Consequently, the ratio of recovery of acetone is not satisfactory, and the acetone content of the bottoms increases to increase COD (chemical oxygen demand) of the effluent.

The present inventors investigated the cause of de-condensation of the condensates during the distillation of the pre-treated crude acetone to form aldehydes again. The investigation has led to the discovery that in the absence of an alkali, the condensation reaction of aldehydes and the de-condensation reaction of the resulting condensates are an equilibrium reaction, and because the aqueous alkali solution used in the pre-treatment is present during the distillation of the pre-treated crude acetone, the equilibrium at the column bottom is shifted to the direction of the de-condensation reaction owing to heating, a lower ketone concentration, a higher concentration of aldol condensates, and a higher water concentration and therefore that so long as an aqueous alkali solution is used in pre-treating crude acetone, distillation of the pre-treated crude acetone at an elevated distillation temperature for a higher ratio of recovery of acetone necessarily leads to formation of the aldehydes which will get mixed with the purified acetone.

If instead of the aqueous alkali solution, a solid alkali is used in the pre-treatment of the crude acetone and is removed before the pre-treated crude acetone is submitted to distillation, the aforesaid defect would be removed. Investigations of the present invention have shown that when a particulate alkali metal hydroxide such as particulate sodium hydroxide is used as the solid alkali to treat crude acetone which contains a small amount of water for some reason or other, the sodium hydroxide will absorb the water and undergo deliquescence, and that if the crude acetone is pre-treated with the particulate alkali metal hydroxide by an industrially preferred method which comprises passing the crude ketone through a fixed bed packed with the particulate alkali metal hydroxide, the particulate sodium hydroxide cannot retain its good shape, or dissolves to form a concentrated aqueous alkali solution which induces de-condensation of aldols in the subsequent distilling step and leads to the inclusion of aldehydes in the recovered acetone. Hence, this method cannot be satisfactorily employed in industrial practice.

It was further found that when other solid alkalies, for example the oxide or hydroxide of an alkaline earth metal such as calcium oxide, magnesium oxide, calcium hydroxide, magnesium hydroxide and barium hydroxide, potassium carbonate and sodium carbonate, are used, the condensation of aldehydes to aldols is slow and is not feasible for industrial application.

The present inventors previously proposed, as an improvement of the method using a solid alkali, a process for purifying a ketone which comprises heating a crude ketone containing traces of aldehydes in the presence of an anion exchange resin having a hydroxyl-type quaternary ammonium salt site, and then distilling the heated crude ketone (Japanese Laid-Open Patent Publication No. 137907/78). This process, however, has the defect that a trace of an amine formed by dissociation of the ammonium salt of the anion exchange resin sometimes gets mixed with the final acetone product.

It is an object of this invention to provide a process for purifying a crude ketone containing trace of aldehydes, which is free from the aforesaid defects.

More specifically, it is an object of this invention to provide a solid alkali composition for use in pre-treating a crude ketone, especially crude acetone, containing traces of aldehydes to convert the aldehydes to high boiling compounds (aldols), which can convert the aldehydes to the high boiling compounds at a commercially feasible rate, does not change in shape even when the pre-treatment is performed for an extended period of time, and which does not flow into the treated ketone. It is also an object of this invention to provide an improved process suitable for industrial practice which can afford a purified ketone substantially free from aldehydes by simply distilling the crude ketone pretreated with the aforesaid solid alkali composition.

It has now been found surprisingly that when a crude ketone is pre-treated with a three-component solid alkali composition composed of an alkali metal oxide and/or hydroxide, an alkaline earth metal oxide and/or hydroxide and silicon dioxide in the proportions specified hereinbelow, the aldehydes in the crude ketone can be easily condensed to high boiling compounds, the solid alkali composition does not change in shape even when the pre-treating operation is carried out for an extended period of time, and that in spite of the presence of the alkali metal oxide and/or hydroxide in the solid alkali composition, the solid alkali does not dissolve in the crude ketone containing a small amount of water.

Thus, the present invention pertains, in a process for recovering a purified ketone substantially free from aldehydes which comprises contacting a crude ketone containing small amounts of aldehydes with an alkali and then distilling the treated crude ketone, to the improvement wherein said alkali is a solid alkali composition composed of an alkali metal compound selected from alkali metal oxides and hydroxides, an alkaline earth metal compound selected from alkaline earth metal oxides and hydroxides and silicon dioxide in which the mole ratio of the alkali metal to the alkaline earth metal is in the range of from 1:1 to 1:15, and the mole ratio of the alkali metal to silicon is in the range of from 1:0.25 to 1:5.

According to the process of this invention, by simply passing a crude ketone containing traces of aldehydes through a fixed bed packed with the solid alkali composition in the form, of, for example, particles, the aldehydes are easily condensed to high-boiling compounds, and even when a small amount of water is present in the pre-treated crude ketone, the alkali does not dissolve in it, and subsequent simple distillation of the pretreated crude ketone gives a purified ketone substantially free from the aldehydes. Another advantage is that when a crude ketone containing a small amount of water is treated over a long period of time, scarcely any change in the shape of the solid alkali is noted, and the solid alkali can withstand long-term use.

The greatest characteristic feature of the present invention is that a crude ketone is pre-treated with a solid alkali composition having the above-specified constituents and proportions.

The solid alkali composition used in accordance with this invention is composed of (a) at least one alkali metal compound selected from alkali metal oxides and hydroxides, (b) at least one alkaline earth metal compound selected from alkaline earth metal oxides and hydroxides, and (c) silicon dioxide.

Examples of the alkali metal are lithium, sodium, and potassium. Sodium is preferred. The alkali metal oxides or hydroxides include, for example, lithium oxide, sodium oxide, potassium oxide, sodium hydroxide, and potassium hydroxide. These compounds can be used either singly or in combination with each other.

Examples of the alkaline earth metal are magnesium, calcium, strontium and barium. Calcium is most suitable. The alkaline earth metal oxides or hydroxides include, for example, magnesium oxide, calcium oxide, barium oxide, magnesium hydroxide, calcium hydroxides strontium hydroxide and barium hydroxide. These compounds are used either singly or in combination with each other.

Accordingly, a preferred solid alkali composition in accordance with this invention may be composed of sodium oxide and/or sodium hydroxide, calcium oxide and/or calcium hydroxide, and silicon dioxide.

The proportions of these compounds in the solid alkali composition can be determined by the mole ratios of the alkali metal, alkaline earth metal and silicon present in the composition. Specifically, in the solid alkali composition in accordance with this invention, the mole ratio of the alkali metal to the alkaline earth metal is from 1:1 to 1:15, preferably from 1:1.5 to 1:10. The mole ratio of the alkali metal to silicon is from 1:0.25 preferably from 1:0.4 to 1:3.

The solid alkali composition may be prepared, for example, by (i) a method which comprises fully mixing colloidal silica, an alkali metal hydroxide and an alkaline earth metal hydroxide in predetermined proportions in water, and subsequently, drying the mixture at a temperature at which the aforesaid compounds do not melt, for example at 500° C. or below, or (ii) a method involving using an alkali metal silicate such as sodium metasilicate or water glass. Advantageously, it is prepared by the latter method which comprises mixing an alkaline earth metal oxide and/or hydroxide, optionally an alkali metal oxide and/or hydroxide and optionally colloidal silica to an alkali metal silicate such as sodium silicate, especially water glass, so that the mole ratio of the alkali metal to the alkaline earth metal and the mole ratio of the alkali metal to silicon in the mixture are within the above-specified ranges fully mixing them uniformly in water, and then drying the mixture by heating.

The drying temperature is not critical, and can be varied widely depending upon the constituents and proportions of the mixture, etc. Generally, the temperature is the one at which the mixture does not melt, preferably about 500° C. or below. Usually, temperatures of about 100° C. to about 300° C. are advantageously used. The drying is carried out at the above temperature in such a way that when the resulting alkali composition is heated at 210° C. for 30 minutes in a nitrogen atmosphere, its weight loss is not more than 10% by weight, preferably not more than 8% by weight. Advantageously, the drying is carried out in an atmosphere of a gas free from an acidic gas such as carbon dioxide, for example in an atmosphere of nitrogen gas or air removed free of carbon dioxide gas.

The alkali composition so prepared is pulverized, and if desired, molded into a desired shape such as spheres, pellets, and granules.

The crude ketone to be treated by the process of this invention contains as impurities small amounts of aldehydes, especially about 50 to about 1000 ppm (by weight) of aliphatic aldehydes such as acetaldehyde, propionaldehyde, n-butyraldehyde and isobutyaldehyde. Industrially, such a crude ketone is available, for example, as (a) a crude ketone obtained by acid cleavage of the aforesaid aralkyl peroxide and subsequent distillation of the acid-cleavage reaction mixture, such as crude acetone obtained by acid cleavage of cumene hydroperoxide, crude methyl ethyl ketone obtained by acid cleavage of sec-butylbenzene hydroperoxide or crude methyl isobutyl ketone obtained by acid cleavage of methylisobutylphenylmethane hydroperoxide; (b) the IPA method crude acetone obtained by dehydrogenation of isopropyl alcohol; and (c) the Wacker method crude acetone obtained by oxidation of propylene. The process of this invention can be especially advantageously applied to the purification of a crude acetone fraction obtained by acid cleavage of cumene hydroperoxide followed by distilling the acid cleavage reaction product.

The crude ketone to be treated by the process of this invention may permissibly contain up to about 15% by weight of water. When only an alkali metal hydroxide is used as the solid alkali, its function is lost if at least about 0.5% by weight of water is present in the crude ketone. The present invention, however has the advantage that the presence of water in such an amount does not at all affect the performance of the process of this invention. Thus, the crude ketone which can be treated by the present invention may contain up to 15% by weight, preferably up to 5% by weight, of water.

The contacting of the crude ketone with the solid alkali composition in accordance with the process of this invention may be carried out batchwise or continuously. In industrial practice, the continuous operation is preferred.

In the batchwise process, it is convenient to use the solid alkali composition in an amount of usually 0.5 to 100 parts by weight, preferably 2 to 50 parts by weight, per 100 parts by weight of the crude ketone to be treated, and perform the contacting treatment at a temperature from room temperature to 120° C., preferably from 30° to 70° C., for a period of 10 minutes to 5 hours, preferably from 40 minutes to 3 hours, with stirring. An ordinary reactor equipped with a stirrer, a thermometer, a heater, etc. may be used in this process, and no special device is required.

In the continuous process, the crude ketone is passed through a fixed bed packed with the solid alkali composition at a space velocity of from 1 to 50 hr$^{-1}$, preferably from 2 to 20 hr$^{-1}$. The temperature used at this time may be the same as used in the batchwise process. In performing the continuous process, there may be used a reactor having a similar structure to an ordinary packed tower which includes a temperature-controllable heater and has a structure capable of holding the solid alkali composition and permitting flowing of the ketone therethrough.

The pressure at the time of the contacting treatment is not particularly critical, and usually atmospheric pressure or a pressure of up to 10 kg/cm$^2$.G may be used.

The crude ketone thus treated with the solid alkali composition does not substantially contain free aldehydes. The aldehydes are converted as a result of the contacting treatment to high-boiling condensation products composed mainly of aldol condensation products of aldehydes and ketones. Furthermore, since the alkali does not substantially dissolve in the pre-treated ketone, the aldehydes do not dissociate and distill out in the subsequent distilling step, and a purified ketone substantially free from the aldehydes can be obtained stably.

In the step of distilling the pre-treated crude ketone, the degree of pressure reduction is determined according to the type of ketone, and the pre-treated crude ketone is distilled usually at a temperature of 30° to 100° C. to afford a purified ketone at a good ratio of recovery.

In the distilling step, high-boiling fractions are discharged from the bottom of the distillation column, and the high-boiling fractions may sometimes contain a ketone dimer resulting from condensation of the ketone. For example, when the ketone is acetone, diacetone alcohol is formed as a by-product in an amount of about several percent based on the crude acetone charged. Preferably, the ketone dimer is de-condensed to recover the ketone. To achieve this, the high-boiling fraction containing the ketone dimer and the aldehyde condensates is treated in such a manner as to decondense the ketone dimer selectively while substantially inhibiting de-condensation of the aldehyde condensates. This further increases the ratio of recovery of the ketone. The following two methods are recommended as a specific procedure.

One method involves recycling a suitable amount of the high-boiling fraction to the step of treating the crude ketone with the alkali solid alkali composition. According to this method, a ketone corresponding to the recycled ketone dimer is formed almost in the same amount. On the other hand, the aldol condensates of the aldehydes and the ketone as main components of the aldehyde condensation products are partly dissociated into the ketone and the aldehydes. However, since the amount of the ketone is overwhelmingly large in the pretreating system, the equilibrium is shifted in the direction of formation of condensates, and the amounts of the aldol condensates dissociated are negligibly small. Accordingly, the ketone which distills in the subsequent distilling step is substantially free from aldehydes. If substantially all of the high-boiling fraction is recycled, the aldehyde condensation products are concentrated in the recycle system, and de-condensation takes place to an unnegligible degree, and the aldehyde content of the purified ketone increases. Accordingly, the amount of the high-boiling fraction to be recycled is limited. This amount is selected depending upon conditions under which the crude ketone is treated with the solid alkali composition. Generally, it is convenient to recycle about 90 to about 99% by weight of the high-boiling distillation bottoms. If required, water may be removed from the high-boiling distillation bottoms prior to recycling.

Another method comprises adjusting the pH of the high-boiling fraction discharged from the distilling step to 7 to 12 with, for example, sodium hydroxide, potassium hydroxide, sodium carbonate or sodium hydrogen carbonate, and heat-treating it at a temperature of 50° to 100° C. for a period of about 10 minutes to 10 hours whereby diacetone alcohol alone can be selectively dissociated to acetone. After this heat-treatment, the acetone is distilled to recover purified acetone free from aldehydes. This heat-treatment and distillation can be simultaneously performed.

By employing such a procedure, the process of this invention can afford a purified ketone substantially free from aldehydes in a yield of as high as 99% or more.

When the crude ketone is contacted with the same solid alkali composition for a long period of time, the activity of the solid alkali composition gradually decreases and the rate of condensation of the aldehydes in the crude ketone may sometimes decrease, although this depends upon the pre-treating conditions. In such a case, the solid alkali composition may be regenerated. It has been found that the regeneration can be easily performed by dipping the solid alkali composition in a solution of an alkali metal hydroxide. The alkali metal hydroxide that can be used for the regenerating operation may, for example, be lithium hydroxide, sodium hydroxide, potassium hydroxides and the mixtures thereof. In industrial practice, sodium hydroxide is preferred. The concentration of the alkali metal hydroxide in the solution is usually 0.1 to 10 N, preferably 2 to 6 N. If the concentration of the alkali metal hydroxide is lower than 0.1 N, the deactivated alkali composition cannot be sufficiently regenerated. On the other hand, when it is higher than 10 N, the viscosity of the solution increases, or the solution may solidify in cold climate, thus presenting handling difficulties.

The solution of the alkali metal hydroxide may be prepared by using a lower alcohol such as methanol, ethanol or isopropanol, or water, or a mixture of these as a solvent. Water is preferred as the solvent.

Preferably, the regeneration of the alkali composition with the solution of alkali metal hydroxide (to be referred to as the alkali solution) is carried out by the following procedures.

One procedure involves contacting the deactivated alkali composition with an alkali solution kept at a relatively high temperature. Another procedure involves contacting the deactivated alkali composition with a solvent kept at a high temperature, such as alcohols (e.g., methanol, ethanol, isopropanol, butanol), water or a mixture of any two of these, preferably water, and subsequently contacting it with an alkali solution.

The first regenerating procedure comprises dipping the deactivated alkali composition in the alkali solution at about 30° to 120° C., preferably about 50° to about 100° C., for about 10 minutes to about 48 hours, preferably 30 minutes to 24 hours. Desirably, the procedure is operated such that the alkali solution is fully contacted with the deactivated alkali composition. Preferably, this can be achieved by using the alkali solution in an amount which can at least fill the pores of the deactivated solid alkali composition, and allowing the alkali composition to stand in the alkali solution. When the pores are not fully filled with the alkali solution, the regeneration may be achieved by using some amount of the alkali solution and stirring it.

According to the second procedure, the solid alkali composition is treated with a solvent of the type described above which is kept at about 40° to about 170° C., preferably at 70° to 130° C. This treating operation may be carried out batchwise or continuously. In the batchwise treatment, the deactivated solid alkali composition is dipped in the solvent in an amount more than that required to fill the pores of the alkali composition although the amount of the solvent differs depending upon the amount and temperature of the solvent used, etc., and allowed to stand for 10 minutes to 2 hours with or without stirring. Then, the alkali composition is separated by filtration. This operation is repeated a number of times, usually at least three times. The total amount of the solvent used by the repetition of the operation is as described hereinbelow. In the continuous process, the solvent is passed through a fixed bed packed with the deactivated solid alkali composition at a liquid space velocity of about 0.1 to about 40 $hr^{-1}$.

Better results can be obtained by using a large total amount of the solvent. Usually, the total amount of the solvent is at least 10 times, preferably at least 20 times, the apparent volume of the deactivated solid alkali composition. The upper limit is 300 times, preferably 200 times, from the economical viewpoint. According to the second procedure, the treated alkali composition is subsequently treated with the alkali solution. This treatment can be performed satisfactorily at room temperature. Or the temperature employed in the first procedure may be used without modification. Other operating conditions may be the same as those used in the first procedure.

The second procedure gives better results.

After such a treatment is over, the treated alkali composition is separated from the alkali solution, and dried at room temperature by, for example, blowing dry nitrogen.

The regenerated solid alkali composition can again perform its inherent function, and therefore, can again be used in the process of this invention.

The following Examples and Comparative Examples illustrate the present invention more specifically.

EXAMPLE 1

Preparation of a Solid Alkali

A 500 ml stainless steel beaker was charged with 110 g of a 10% aqueous solution of sodium hydroxide, and 50 g of water glass (JIS No. 1) was added to it to form a uniform solution. The solution was poured into a 1-liter stainless steel beaker containing 130 g of calcium hydroxide. They were fully mixed until a uniform solution was obtained. The solution was transferred to a stainless steel vat and dried in a desiccator at 180° to 200° C. for 24 hours in a stream of nitrogen. After the drying, the product was pulverized to a particle size of 10 to 20 mesh. The resulting solid alkali composition was stored in a nitrogen box under a stream of nitrogen.

The solid alkali composition thus prepared was found to contain 7.2% by weight of sodium, 38.5% by weight of calcium and 4.6% by weight of silicon with a Ca/Na mole ratio of 3.1 and an Si/Na mole ratio of 0.52.

Purification of Crude Acetone

A jacketed packed tube (inside diameter 25 mm) was set perpendicularly in order to pass hot water, and 60 ml (40.5 g) of the solid alkali composition was filled into the tube. Crude acetone containing 60 ppm of isobutyraldehyde and 2.7% of water was allowed to flow continuously at a space velocity of 5.2 $hr^{-1}$ and a reaction temperature of 51° C. through the packed layer from top to bottom. The amount of isobutyraldehyde in the reacted acetone on the exit end was less than 1 ppm 24 hours, 48 hours, and 72 hours, respectively.

The treated crude acetone (5 liters) was distilled batchwise in an Oldershaw-type distillation column (20 trays). Acetone was recovered in a ratio of about 93 to 94% from the initial distillate to a fraction distilled at 56.5° C. The amount of the distillation bottoms was 344 g.

The recovered acetone contained less than 1 ppm of isobutyraldehyde. The distillation bottoms contained diacetone alcohol and water as main components.

EXAMPLES 2 TO 4

The same procedure as in Example 1 was performed except that in the preparation of the solid alkali composition in Example 1, the amounts of the sodium hydroxide solution, water glass and calcium hydroxide, and a suitable amount of colloidal silica containing 18.5% of silicon dioxide (Snowtex O, a tradename for a product of Nissan Chemical Co., Ltd.) was used as required to prepare a solid alkali composition having each of the constituent proportions shown in Table 1. The results are also shown in Table 1.

COMPARATIVE EXAMPLES 1 TO 4

Solid alkali compositions having the constituent proportions shown in Table 1 were prepared by the same method as in Example 1, and the same operation as in Examples 2–4 was performed except that only in Comparative Example 4, the acetone after treatment with the solid alkali composition was distilled. The crude acetone to be distilled in Comparative Example 4 was crude acetone obtained after a lapse of about 48 hours in a continuous operation. The results are shown in Table 1.

TABLE 2

| Example (Ex.) or Comparative Example (CEx.) | Solid alkali | Treating conditions Temperature (°C.) | Time (minutes) | Aldehyde content in the treated acetate (ppm) |
|---|---|---|---|---|
| Ex. 5 | Same as that obtained in Example 1 | 50 | 30 | less than 1 |
| Ex. 6 | Same as that obtained in Example 1 | 25 | 30 | less than 1 |
| CEx. 5 | Na$_2$CO$_3$ | 50 | 30 | 52 |
| CEx. 6 | MgO | 50 | 30 | 49 |
| CEx. 7 | K$_2$CO$_3$ | 50 | 30 | 50 |
| CEx. 8 | CaO | 50 | 30 | 51 |
| CEx. 9 | Ca(OH)$_2$ | 50 | 45 | 41 |
| CEx. 10 | Sodium metasilicate | 50 | 30 | less than 1* |

*Note
The treated acetone was distilled to recover acetone in a recovery ratio of 94%. The recovered acetone contained 20 ppm of aldehyde. To the treated acetone was added the same volume of water, and the pH of the aqueous solution was measured and found to be 9.8. In view of the fact that the pH of the untreated acetone in the same volume of water was 7.6, it is seen that the treated acetone contained an alkaline component.

EXAMPLE 7

(A) Two packed towers set perpendicularly and having a diameter of 2 inches and a height of 4.0 m were connected in series, and 7.3 liters of the solid alkali composition prepared in Example 1 was packed into the towers. Crude acetone containing 60 ppm of isobutyraldehyde and 27% by weight of water was passed from top to bottom through the packed layer at a liquid space velocity of 5 hr$^{-1}$ and a temperature of 40° to 60° C. The content of isobutyraldehyde in the acetone discharged from the second packed tower was measured by gas chromatography. The isobutyraldehyde content that changed with the operating time is shown in Table 3.

TABLE 1

| Example (Ex) or Comparative Example (CEs.) | Constituent proportions of the solid alkali composition (% by weight) | | | (mole ratio) | | Aldehyde content (ppm) of acetone after passage through the layer of the solid alkali composition | | | Aldehyde content of acetone after distillation (ppm) | Ratio of recovery of acetone (%) |
|---|---|---|---|---|---|---|---|---|---|---|
| | Na | Ca | Si | Ca/Na | Si/Na | 24 hours later | 48 hours later | 72 hours later | | |
| Ex. 1 | 7.2 | 38.5 | 4.6 | 3.1 | 0.52 | less than 1 | less than 1 | less than 1 | less than 1 | 93–94 |
| Ex. 2 | 3.8 | 43.0 | 5.0 | 6.5 | 1.1 | less than 1 | less than 1 | less than 1 | less than 1 | " |
| Ex. 3 | 2.7 | 43.5 | 5.2 | 9.3 | 1.6 | less than 1 | less than 1 | less than 1 | less than 1 | " |
| Ex. 4 | 2.1 | 40.4 | 5.2 | 11.1 | 2.0 | less than 1 | less than 1 | 3 | less than 1 | " |
| CEx. 1 | 4.2 | 54.6 | 0 | 7.5 | 0 | less than 1 | 6 | 9 | — | — |
| CEx. 2 | 1.4 | 40.8 | 4.8 | 16.8 | 2.8 | 3 | 7 | 15 | — | — |
| CEx. 3 | 0.2 | 37.0 | 5.3 | 106 | 22 | 34 | 58 | 58 | — | — |
| CEx. 4 | 21.2 | 18.4 | 12.9 | 0.5 | 0.5 | less than 1 | 3 | 7 | 20 | — |

EXAMPLES 5 AND 6

Five (5) grams of the solid alkali composition prepared in Example 1 was added to 100 ml of crude acetone containing 60 ppm of isobutyraldehyde and 3.0% by weight of water was put into a 300 ml flask equipped with a stirrer, a thermometer, a condenser and a sampling hole. The crude acetone was thus treated with stirring for 30 minutes at a temperature of 50° C. (Example 5) or 25° C. (Example 6). The content of isobutyraldehyde in the crude acetone after the treatment is shown in Table 2.

COMPARATIVE EXAMPLES 5 TO 10

The same procedure as in Example 5 was repeated except that each of the solid alkalies shown in Table 2 was used, and the treating temperature and time were changed as shown in Table 2. The results are shown in Table 2.

TABLE 3

| Operating time (days) | Content of isobutyraldehyde in the discharged acetone (ppm) |
|---|---|
| 1 | 0 |
| 5 | 0 |
| 10 | 0 |
| 15 | 0 |
| 20 | 0 |
| 25 | 6 |

TABLE 3-continued

| Operating time (days) | Content of isobutyraldehyde in the discharged acetone (ppm) |
| --- | --- |
| 30 | 14 |

(B) After the 30 day-operation in the treatment described in (A) above, hot water at 80° to 95° C. was passed at a flow rate of 250 liters/hour through the solid alkali composition-packed layer from top to bottom for 2.5 hours. Then, a suitable amount of nitrogen was caused to flow through the packed layer from top to bottom. When no water drop was seen to fall from the bottom of the packed layer, nitrogen was further fed into the packed layer to dry it for a day and night. Then, a 4 N aqueous solution of sodium hydroxide was filled into the packed layer, and the packed layer was allowed to stand for 15 hours. The liquid was removed, and the packed layer was dried with nitrogen by the same method as above. Then, crude acetone was passed through the packed layer in the same way as above. The isobutyraldehyde content with the operating time is shown in Table 4.

TABLE 4

| Operating time (days) | Content of isobutyraldehyde in the discharged acetone (ppm) |
| --- | --- |
| 1 | 0 |
| 5 | 0 |
| 10 | 0 |
| 15 | 0 |
| 20 | 6 |
| 25 | 7 |

(C) The solid alkali composition whose activity decreased as a result of a 25-day operation was again regenerated by the method described in (B) above, and subsequently, crude acetone was caused to flow through the packed layer in the same way as above. The isobutyraldehyde content with the operating time is shown in Table 5.

TABLE 5

| Operating time (days) | Isobutyraldehyde content in the discharged acetone (ppm) |
| --- | --- |
| 1 | 0 |
| 5 | 0 |
| 10 | 0 |
| 15 | 0 |
| 20 | 4 |
| 25 | 9 |

The results show that the solid alkali composition in accordance with this invention can be repeatedly used by regeneration.

EXAMPLE 8

The same procedure as in Example 7, (B) was repeated except that a 3 N aqueous solution of potassium hydroxide was used instead of sodium hydroxide. The results are shown in Table 6.

TABLE 6

| Operating time (days) | Isobutyraldehyde in the discharged ketone (ppm) |
| --- | --- |
| 1 | 0 |
| 5 | 0 |
| 10 | 0 |
| 15 | 0 |
| 20 | 5 |
| 25 | 7 |

EXAMPLE 9

Preparation of a Solid Alkali

Three hundred (300) grams of sodium metasilicate was put into a 2-liter stainless steel beaker containing 600 ml of distilled water, and then 100 g of calcium hydroxide was added. They were well mixed. The mixture was then worked up in the same way as in Example 1 except that the drying was carried out at 120° to 130° C. for 72 hours to form a solid alkali composition containing 7.6% by weight of sodium, 36.1% by weight of calcium and 4.8% by weight of silicon with a Ca/Na mole ratio of 2.72 and an Si/Na mole ratio of 0.52.

Purification of Crude Acetone

Crude acetone was purified in the same way as in Example 1 except that the solid alkali composition prepared as above was used. The amount of isobutyraldehyde in the reacted acetone on the exit side was less than 1 ppm 24 hours, 48 hours, and 72 hours later, respectively. By distilling the pre-treated crude acetone, acetone was recovered in a ratio of about 93 to 94% from fractions ranging from the initial distillate to a fraction at 56.5° C.

What we claim is:

1. In a process for recovering a purified ketone substantially free from aldehydes which comprises contacting a crude ketone containing small amounts of aldehydes with an alkali and then distilling the treated crude ketone, the improvement wherein said alkali is a solid alkali composition composed of an alkali metal compound selected from alkali metal oxides and hydroxides, an alkaline earth metal compound selected from alkaline earth metal oxides and hydroxides and silicon dioxide in which the mole ratio of the alkali metal to the alkaline earth metal is in the range of from 1:1 to 1:15, and the mole ratio of the alkali metal to silicon is in the range of from 1:0.25 to 1:5.

2. The process of claim 1 wherein said alkali metal compound is a sodium compound.

3. The process of claim 1 wherein said alkaline earth metal compound is a calcium compound.

4. The process of claim 1 wherein said alkali composition is prepared by adding at least one member of the group consisting of an alkaline earth metal oxide, an alkaline earth metal hydroxide, and an alkali metal oxide, an alkali metal hydroxide, and colloidal silica to an alkali metal silicate so that the mole ratio of the alkali metal to the alkaline earth metal and the mole ratio of the alkali metal to the silicon are within the specified ranges, fully mixing these compounds in water to form a uniform mixture, and then drying the mixture at an elevated temperature.

5. The process of claim 4 wherein the drying of the mixture is carried out at a temperature of not more than about 500° C.

6. The process of claim 1 wherein the mole ratio of the alkali metal to the alkaline earth metal is from 1:15 to 1:10.

7. The process of claim 1 wherein the mole ratio of the alkali metal to silicon is in the range of from 1:0.4 to 1:3.

8. The process of claim 1 wherein said crude ketone contains 50 to 100 ppm by weight of aliphatic aldehydes.

9. The process of claim 1 wherein said crude ketone may contain up to 15% by weight of water.

10. The process of claim 1 wherein said ketone is acetone.

11. The process of claim 1 wherein said crude ketone is a crude acetone fraction obtained by acid cleavage of cumene hydroperoxide and subsequent distillation of the cleavage reaction product.

* * * * *

UNITED STATES PATENT AND TRADEMARK OFFICE
CERTIFICATE OF CORRECTION

PATENT NO. : 4,329,510
DATED : May 11, 1982
INVENTOR(S) : Uno, et al.

It is certified that error appears in the above—identified patent and that said Letters Patent is hereby corrected as shown below:

Claim 8, line 2, "100" should be --1000--.

*Signed and Sealed this*

*Twenty-fourth* Day of *August 1982*

[SEAL]

Attest:

GERALD J. MOSSINGHOFF

*Attesting Officer*   *Commissioner of Patents and Trademarks*